United States Patent [19]

Franck et al.

[11] Patent Number: 5,085,087
[45] Date of Patent: Feb. 4, 1992

[54] SAMPLING CORROSIVE FLUID

[75] Inventors: Gerhard Franck, Frankfurt; Guenter Rumpf, Weilrod, both of Fed. Rep. of Germany

[73] Assignee: Hartmann & Braun AG, Frankfurt am Main, Fed. Rep. of Germany

[21] Appl. No.: 550,285

[22] Filed: Jul. 9, 1990

[30] Foreign Application Priority Data

Jul. 15, 1989 [DE] Fed. Rep. of Germany ....... 3923544

[51] Int. Cl.⁵ .............................................. G01N 1/22
[52] U.S. Cl. .............................. 73/864.73; 73/863.81
[58] Field of Search .................... 73/864.73, 864.74, 863.81–863.86, 73/863.11, 863.12, 866.5

[56] References Cited

U.S. PATENT DOCUMENTS 3,714,565 1/1973 Coulter et al. .................. 324/71.1
4,061,135 12/1977 Widren et al. ...................... 128/6
4,379,412 4/1983 Wood ........................ 73/864.73 X
4,756,200 7/1988 Ramsner et al. ............ 73/864.73 X

FOREIGN PATENT DOCUMENTS 3305232 8/1984 Fed. Rep. of Germany.
248658 8/1987 German Democratic Rep. ............................... 73/864.73

Primary Examiner—Tom Noland
Attorney, Agent, or Firm—R. H. Siegemund

[57] ABSTRACT

A sampling device for sampling a corrosive medium, is comprised of an inner tube with a flange and an outer tube with a flange, both made of a synthetic material; a metallic tube with flange is interposed between the inner and outer tubes to serve as armoring in this coaxial synthetic tube arrangement; the flange of the metal tube grips around the flange of the outer tube; and a recess in one of the synthetic flanges exposes a portion of the metal flange of the intermediate tube as a support surface for a fastening structure.

1 Claim, 1 Drawing Sheet

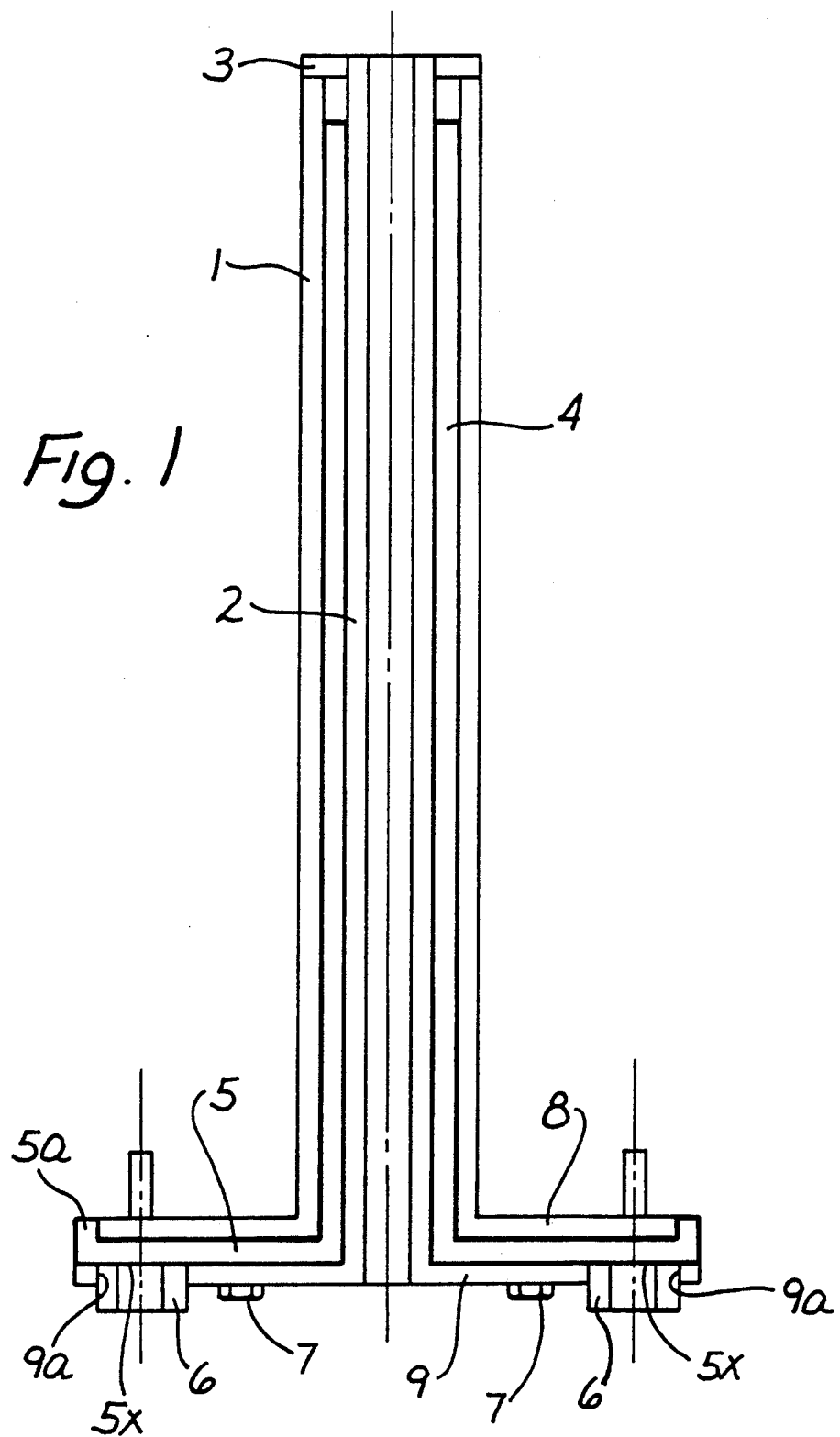

SAMPLING CORROSIVE FLUID

BACKGROUND OF THE INVENTION

The present invention relates to a sampling probe for sampling fluids, particularly corrosive fluids and more particularly the invention relates to a sampling device including an inner tube with a flange both made of a synthetic material and an outer tube, also with a flange also made of synthetic material.

A sampling device of the type and kind to which the invention pertains is shown e.g. in German patent 33 05 232. This patent describes a device for taking a hot gas sample from a particular volume of gases, under utilization of a sampling device that can be inserted through an opening in the wall structure confining the gas to be sampled. Moreover a guide tube (4) is secured to that particular wall in the aforementioned opening, for guiding the tubular sampling device. Flange structure is provided at the outer end of that guide tube but in a spaced relation to the wall, and the jacket of the sampling device is releasably secured to that flange. This being the basic structure serving as a point of departure as far as the present invention is concerned. The following should be considered. Genuinely representative sampling of a particular volume often requires to use long sample devices, particularly to reach far in the interior of whatever is being sampled. Depending on the construction and the structural features as they exist it is not always possible to suspend from above the sampling into the volume containing the sampling material. In some cases it may be absolutely necessary to introduce the sample structure laterally i.e. horizontally.

It is very clear, that owing to the inherent weight of the sampling structure there is a certain bending load which is particularly effective as a strong shear load right at the transition between sampling device and fastening flange. This static load may actually be increased owing to the flow speed of the medium and in the case the flow through the sample device is no laminar and smooth, dynamic forces will be experienced, and they pose a superimposing load on the sampling tube.

If the samples taken include corrosive components it is necessary to use fiber reinforced synthetic material for the construction of sample structures, but the mechanical strength of fiber reinforced synthetic is limited to other requirements, particularly where constructions with complex geometries are invloved or just large scale structures have become necessary. One can also use metallic sample devices which are coated with synthetic material. It is assumed then that the coat is pore-free but the mechanical protection is insufficient for many fields of use.

DESCRIPTION OF THE INVENTION

It is an object of the present invention to provide a new and improved sampling device particularly for taking samples of corrosive materials such that the components coming in direct contact with a corrosive medium is corrosionproof as commonly expected and realized with sample devices made of synthetic material, while on the other hand the mechanical strength and capability of bending loads of the sample device meets the capabilities of metal tubing.

It is a particular object of the present invention to provide a new and improved sample device for sampling of corrosive medium which device is comprised of an inner tube made of synthetic material as well as of an outer tube each having a flange made also of synthetic material.

In accordance with the preferred embodiment of sthe present invention the objects are attained by interposing in between the synthetic inner tube and the synthetic material outer tube, an intermediate tube with a flange made of metal such that the flange of the intermediate tube circumscribes the flange of the outer tube and fastening structure bears against the flange of the intermediate tube.

BRIEF DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 illustrates a preferred embodiment of the present invention for practicing the best mode thereof showing specifically a sampling device in cross section.

DETAILED DESCRIPTION

Proceeding now to the detailed description of the drawings, the sampling device which is the subject matter of this invention is composed of three telescoping, coaxially arranged tubes. There is accordingly an inner tube 2 which is in fact the flow tube for the sample to be taken, and the interior of that tube 2 will be in a flow conductive relationship with whatever medium is to be sampled. For purposes of protection there is an outer tube 1 circumscribing inter alia the inner tube and in between the tubes 1 and 2 is interposed an intermediate tube 4.

Each of the tubes is provided with a flange and they are accordingly, flange 5 pertaining to and being integral with the intermediate tube 4; there is a flange 8 pertaining to and being integral with the outer tube 1 and and there is a flange 9 which pertains and is an integral part of inner tube 2. Owing to the integral construction it is clear that in such each instance the tube and the respectively interconnected flange are made of the same material.

In the present example the outer tube 1 as well as the tube 2 are made of synthetic; the selection criteria being that of an enhanced corrosionproofness under elevatd temperature and here polytetrafluoroethylene or polyidenfluoride may be used. The two synthetic tubes 1 and 2 are interconnected at the sampling end through connecting ring 3. They are preferably each welded to that ring. The wall thickness in each case is to be sufficiently high so that a diffusion of any corrosive components passing through the sampling tube 2 will not effect the intermediate metal armoring.

As stated the intermediate tube 4 with welded on flanges is made of metal and preferably this construction is made of stainless steel. The metal flange is provided such that clamping obtains vis-a-vis the flange 8 of the outer tube 1. As can be seen specifically from the figure the flange 5 is configured along its periphery as a shallow trough with an up bent rim 5a. This gives the flange a pan-like appearance and the flange 8 of the outer tube is received in that pan.

The flange connection includes further fastening structure, basically a screw connection and they are provided to offer as a support an exposed portion of the metal flange 5. Specifically one can interpret 9a as openings or as recesses in general, receiving, on one hand, a fastening structure 6 while in effect in each instance exposing a portion 5x of the surface of the flange 5 so as to serve as direct abutment for fastening not just of the flange 5 but of the sampling device as a whole.

The two synthetic flanges 8 and 9 are separately connected through fastening means 7 to the flange 5 while the fastening 6 is provided for fastening the sample structure to whatever support and wall structure is present in relation to which the device is to operate.

The invention is not limited to the embodiments described above but all changes and modifications thereof, not constituting departures from the spirit and scope of the invention, are intended to be included.

We claim:
1. Sampling device for sampling a corrosive medium, being comprised of an inner tube with a flange and an outer tube with a flange, the improvement comprising:
   a metallic tube with a flange interposed between the inner and outer tubes, the inner and outer tubes with their respective flanges being made of synthetic material so that the metal intermediate tube serves as armoring being interposed between a coaxial synthetic tube arrangement as composed of said inner and outer tube;
   the flange of the metal tube gripping around the flange of the outer tube; and
   recess means provided in at least one of said synthetic flanges to expose a portion of the metal flange of the intermediate tube as support surfaces for fastening structure.

* * * * *